United States Patent [19]
Farzin-Nia et al.

[11] Patent Number: 5,126,094
[45] Date of Patent: Jun. 30, 1992

[54] HEAT TREATMENT OF AN ORTHODONTIC BRACKET

[76] Inventors: Farrokh Farzin-Nia, 141 W. Fairview Blvd., Inglewood, Calif. 90302; Terry L. Sterrett, 5302 Abbeyfield, Long Beach, Calif. 90815

[21] Appl. No.: 595,633

[22] Filed: Sep. 26, 1990

Related U.S. Application Data

[63] Continuation of Ser. No. 319,987, Mar. 2, 1989, abandoned.

[51] Int. Cl.$^5$ ............................................. B29C 71/02
[52] U.S. Cl. ................................. 264/346; 264/345
[58] Field of Search ............... 264/345, 346, 234, 235

[56] References Cited

U.S. PATENT DOCUMENTS

| | | | |
|---|---|---|---|
| 2,203,182 | 6/1940 | Rendall | 264/346 |
| 2,659,105 | 11/1953 | Halbig et al. | 264/346 |
| 3,723,593 | 3/1973 | Ono | 264/346 X |
| 3,792,139 | 2/1974 | Weinstein | 264/346 X |
| 3,887,524 | 6/1975 | Kirchner et al. | 264/67 X |
| 3,897,529 | 7/1975 | Carr et al. | 264/346 X |
| 3,903,225 | 9/1975 | Jones et al. | 264/234 X |
| 3,939,035 | 2/1976 | Keller | 264/346 X |
| 4,528,275 | 7/1985 | Hodge | 264/346 X |
| 4,595,598 | 6/1986 | DeLuca et al. | 427/2 |
| 4,627,948 | 12/1986 | Zepter et al. | 264/346 X |
| 4,639,218 | 1/1987 | Jones et al. | 433/8 |
| 4,681,538 | 7/1987 | DeLuca et al. | 433/9 |
| 4,703,024 | 10/1987 | Aronov | 264/346 X |

OTHER PUBLICATIONS

"Fracture-Strength Antisotropy of Sapphire", Pual F. Becher, Jan.-Feb. 1976, pp. 59-61, UMI.
"The Influence of Annealing on the Strength of Corundum Crystals", A. H. Heuer & J. P. Roberts, pp. 17-27.
"The Effect of Heat Treatment on the Tensile Strength of Sapphire", L. M. Davies, pp. 29-35.
"Preparation of High-Strength Sapphire Crystals", F. P. Mallinder & B. A. Proctor, pp. 9-16.

Primary Examiner—Jan H. Silbaugh
Assistant Examiner—Karen Aftergut

[57] ABSTRACT

A crystalline orthodontic bracket which has been subjected to a machining operation having improved fracture toughness and a heat treatment method for obtaining such improved fracture toughness. The method includes the steps of placing the machined orthodontic bracket in an oven and heating the bracket at an elevated temperature above normal annealing temperatures and slightly below the melting point of the brackets which is capable of healing surface microcracks. The bracket is maintained at this temperature for a predetermined period of time so as to heal microcracks on the surface. The bracket is then removed and allowed to cool to room temperature.

11 Claims, 5 Drawing Sheets

HEAT TREATMENT OF AN ORTHODONTIC BRACKET

This is a continuation-in-part, of application Ser. No. 07/319,987, filed Mar. 2, 1989, now abandoned.

FIELD OF THE INVENTION

The present invention is directed to crystalline orthodontic brackets having improved fracture toughness, and a method for making same.

BACKGROUND OF THE INVENTION

Recently in the field of orthodontics, it has become very desirable to wearers of orthodontic brackets to have visually asthetic brackets that are clear or substantially transparent. In response to this need, brackets made of crystalline materials have been introduced. While these materials are asthetically appealing, the breakage of brackets made of these type materials has become a problem.

It is well known that the surface condition of a crystalline orthodontic bracket has a direct effect on its strength particularily with a single crystal bracket. Machining operations, such as diamond wheel grinding, have been shown to effect the fracture strength of the material, primarily due to the introduction of flaws at or near the surfaces that have been machined. Surface flaws that result from conventional machining processes typically are scratches and cracks. Additionally, it is believed that conventional machining methods result in residual surface stresses which also decrease the fracture strength. It has been suggested in the prior art that certain heat treatments can be conducted prior to machining, such as discussed in U.S. Pat. Nos. 4,595,598; 4,639,218; and 4,681,538. It has also been suggested that single crystal alumina orthodontic bracket can obtain increased fracture toughness by post-heat treatment. However, these heat treatments merely relieve residual stresses. These heat treatments do nothing to mend or heal the cracks or flaws formed at the surface.

Applicants have invented an orthodontic bracket having improved fracture toughness which is obtained by subjecting the orthodontic bracket to an improved post-heat treatment process whereby not only the residual stresses are relieved, but healing of micro surface flaws is accomplished.

SUMMARY OF THE INVENTION

In the present invention there is provided a crystalline orthodontic bracket having improved fracture toughness and the method of making same comprising the steps of:
a) placing the bracket in an oven and heating the bracket to an elevated temperature just below the melting point of the crystalline bracket;
b) maintaining the bracket at the elevated temperature for a sufficient period of time to heal microcracks on the surface of the bracket; and
c) cooling the bracket.

DETAILED DESCRIPTION OF THE INVENTION

Figure 1:
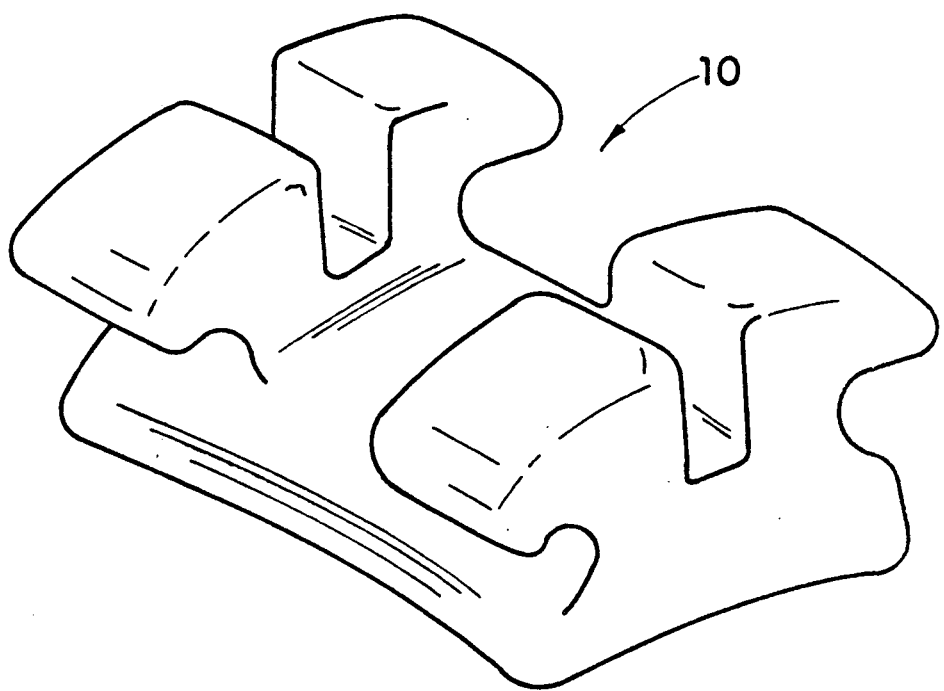
FIG. 1 is a perspective view of an orthodontic bracket made in accordance with the present invention.

Referring to FIG. 1, there is illustrated an orthodontic bracket 10 made of a crystalline material made in accordance with the present invention. In the particular embodiment illustrated, the orthodontic bracket 10 is made of single crystal alumina. However, it is to be understood that other crystalline materials may be used, for example, but not limited to, yttrium alumina garnet, magnesium alumina spinal, and alpha-alumina. Additionally, while the present invention is particularly useful in treating single crystalline material, it is believed that polycrystalline material would also benefit.

The crystalline orthodontic bracket 10 may be made in any desired manner. For example, in U.S. Pat. Nos. 4,595,598 and 4,639,218, and 4,681,538, the orthodontic brackets are made by producing a crystalline alpha alumina rod having a predetermined cross-sectional configuration using the EFG (Edge-defined Film-fed, Growth) process. The rod is then cut into individual blanks and subjected to a series of cutting, grinding, and polishing steps using known technology. Alternatively, the orthodontic bracket 10 may be made in any other desired manner. For example, using ultrasonic machining techniques as described in copending U.S. patent application, Ser. No. 230,759, filed Aug. 10, 1988, now U.S. Pat. No. 4,933,418, which is hereby incorporated by reference. Briefly, the ultrasonic machining technique for producing orthodontic brackets comprises initially cutting a plurality of individual eaches (blanks) from a disc of single crystal alumina. These individual eaches are then subjected to additional ultrasonic machining to form the final bracket configuration.

Figure 2:
FIG. 2 is an enlarged microphotograph of a side view of a single crystalline orthodontic bracket which has been subjected to machining by diamond wheel grinding.

Referring to FIG. 2, there is illustrated a microphotograph of an orthodontic bracket made of single crystal aluminum which has been machined by diamond wheel grinding. This photograph illustrates the presence of cracks which are formed by the grinding operation. In addition to the cracks, stress concentrations are illustrated by birefrigent lines in the photo.

Figure 3:
FIG. 3 is a microphotograph of a single crystalline orthodontic bracket similar to FIG. 1 which has been subjected to ultrasonic machining.

Referring to FIG. 3, there is illustrated a microphotograph of an orthodontic bracket made of single crystal aluminum bracket which has been machined using ultrasonic machining techniques. The intensity of the cracks and scratches in this orthodontic bracket is substantially less than in the diamond wheel grinding of FIG. 2 as expected.

Figure 4:
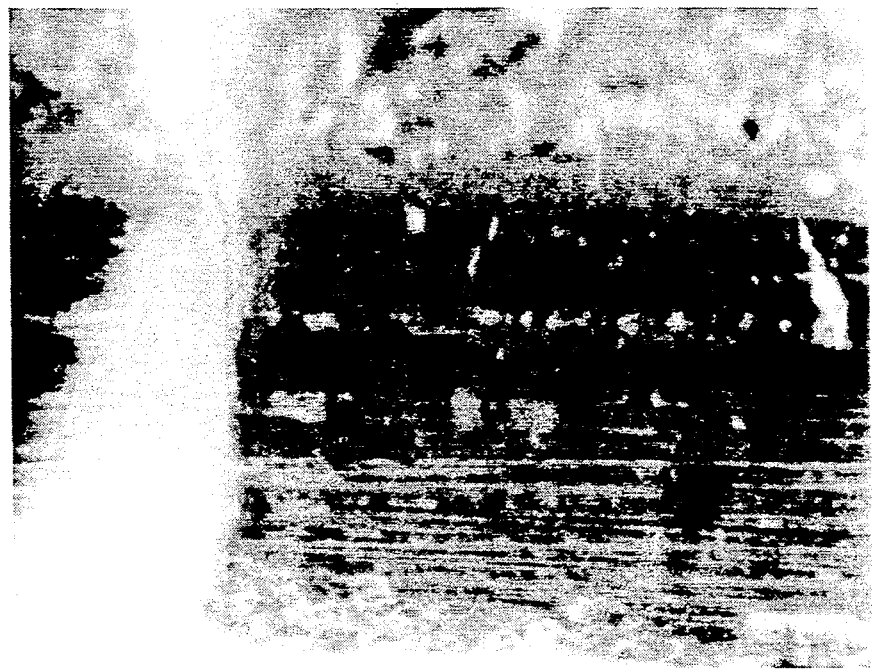
FIG. 4 is a front elevational view of a surface of an orthodontic bracket illustrating the surface which has been machined by a diamond wheel grinding.
Figure 5:
FIG. 5 is a micrograph of the same portion of an orthodontic bracket of FIG. 3 after it has been subjected to heat treatment process according to the present invention.

Referring to FIG. 4, there is illustrated a microphotograph of an orthodontic bracket illustrating a machined area produced by diamond wheel grinding. This figure clearly illustrates a plurality of horizontal grinding streaks formed by the grinding wheel.

Figure 6:
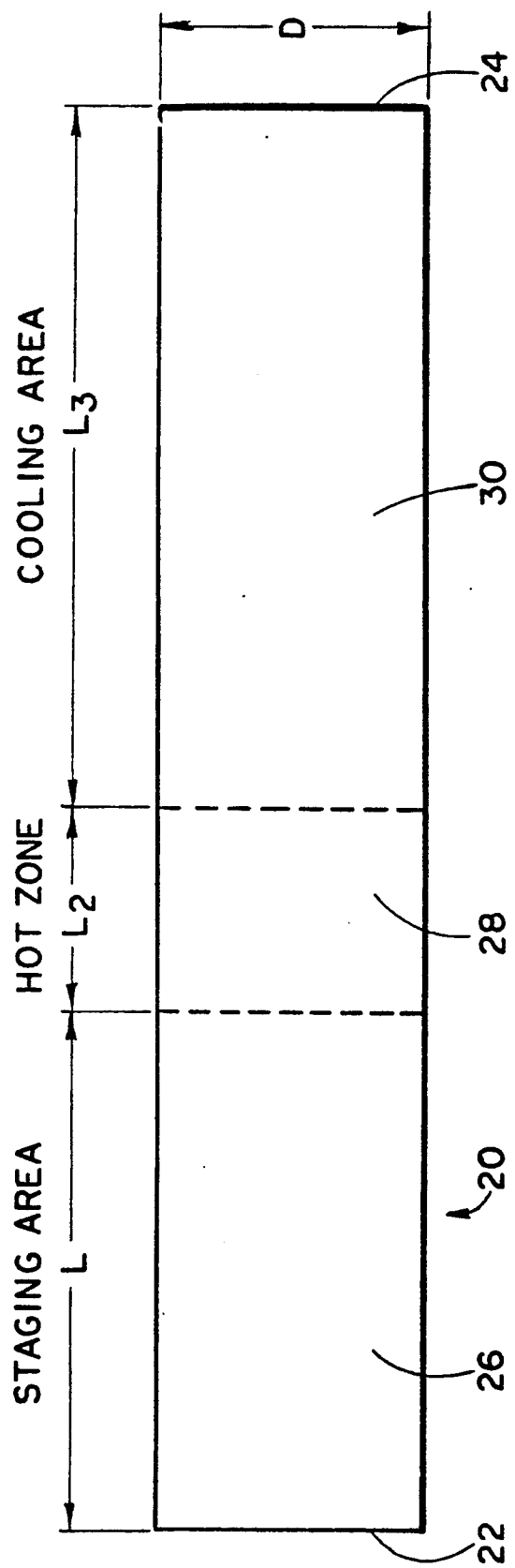
FIG. 6 is a diagramatic representation of a furnace used to heat treat the orthodontic bracket of FIG. 1.

After the orthodontic bracket 10 has been machined to the final desired configuration, it is then subjected to a post-heat treatment process according to present invention whereby the fracture toughness of the orthodontic bracket is improved. The heat treatment process comprises first placing the orthodontic bracket 10 in an oven furnace 20 as illustrated in FIG. 6 which has been preheated to a temperature slightly below the melting temperature of the bracket. Any suitable oven capable of achieving the desired temperature may be used. For example, it is believed that an oven sold by C.M. Furnaces, Inc. under the 400 Series Tungsten Tube Furnace would be quite suitable. Referring to FIG. 6, there is illustrated in diagramatic form furnace 20 used to heat treat bracket 10. Furnace 20 comprises a generally cylindrical tube body having a length of about 87 inches and cross sectional diameter D of about 1.5 inches. The furnace 20 includes an inlet 22 through which brackets are inserted into the furnace and an outlet 24 through which the brackets are removed. Furnace 20 is divided into three sections; a staging area 26, having a length L adjacent to inlet 24, a hot zone 28 having a length L2 adjacent staging area 26 and a cooling area 30 having a length L3 adjacent to the other side of hot zone 28. The staging area 20 is the area in the furnace wherein the articles are initially placed so as to bring the articles slowly up to temperature. The hot zone 28 is the area which the articles are subjected to the preselected temperature and the cooling zone 30 is the area where the product is allowed to cool. In the particular embodiment illustrated, staging area has a length L of about thirty (30) inches, hot area has a length L2 of about twelve (12) inches and cooling area 30 has a length L3 of about forty-five (45) inches. As previously noted, the orthodontic bracket 10 in the embodiment illustrated, is made of single crystal alumina. This material has a melting temperature in the range of 2050° C. Therefore, the temperature of the hot zone 20 is elevated to a temperature of at least 1875° C. It is extremely important that the temperature be sufficiently high in order to obtain the desired healing of microcracks. Temperatures less than 1875° C. for single crystal alumina have been found to be totally inadequate for effecting healing regardless of the length of exposure time. Preferably oven temperatures greater than 1900° C. are used for single crystal alumina. Also the elevated temperature should not be too close to the melting point, as handling of the bracket becomes extremely difficult and a greater risk of melting is present. Preferably the elevated oven temperature is no greater than 1950° C. for brackets made of single crystal alumina. This elevated temperature is higher than the temperatures normally associated with heat treatments which are used simply to relieve residual stresses. Typically prior art heat treatments reach temperatures no greater than about 1850° C. for single crystal alumina. The orthodontic bracket 10 is placed in a container, which is typically referred to as a "boat" and then placed into the oven in a staging area 24 at an area having a temperature of about 1000° C. The orthodontic bracket 10 is maintained in this staging area 26 for approximately 5 minutes. Because of the very small size of the brackets 10, the brackets 10 take about a minute to reach the temperature of the furnace in the staging area 20. Preferably the bracket 10 is heated at a rate of not less than 200° C./minute. Thereafter, the orthodontic bracket is moved into the hot zone 28 of the furnace 20 wherein the temperature is at the preselected temperature, preferably at a temperature of approximately 1925° C. The orthodontic bracket 10 is maintained in this zone for a predetermined period of time so as to heal microcracks on the surface of the orthodontic bracket 10. The bracket is maintained at the elevated temperature for at least 4 hours. For the purposes of the present invention, the healing of microcracks shall mean surface flaws or cracks having a dimension of less than about 0.00025 inches which are either reduced in size or substantially eliminated. Typically, the bracket 10 is maintained at the elevated temperature for a period from about 4 to 12 hours, preferably of about 6 hours. After the orthodontic bracket 10 has been maintained at this elevated temperature, it is removed from the hot zone 28 into cooling section 30 for about five minutes. Thereafter, the bracket 10 is completely removed from the oven and allowed to rapidly cool to room temperature. Preferably the bracket 10 is cooled at a rate of not less than 100° C./minute. It is believed that rapidly cooling of the orthodontic bracket contributes to providing the improved fracture toughness of the article.

Applicants have found that surface cracks up to about 0.00025 inches have been healed or substantially reduced in size when subjected to a heat treatment in accordance with the present invention. This healing has translated to improved fracture toughness. In order to more fully appreciate the benefits of the present invention, fracture toughness of a single crystal-alumina test specimens subjected to a heat treatment according to the present invention were compared to identical specimens with no heat treatment and specimens having a heat treatment according to the prior art type.

The test results were obtained using identical test specimens. The specimens possessed a rectangular configuration with the following dimensions; 0.23 cm × 0.23 cm × 2.54 cm. Calculation of fracture toughness was done in accordance with ASTM E399. The notches in the specimens were formed by three different machining operations; diamond wheel griding, diamond filing and ultrasonic machining.

Figure 7:
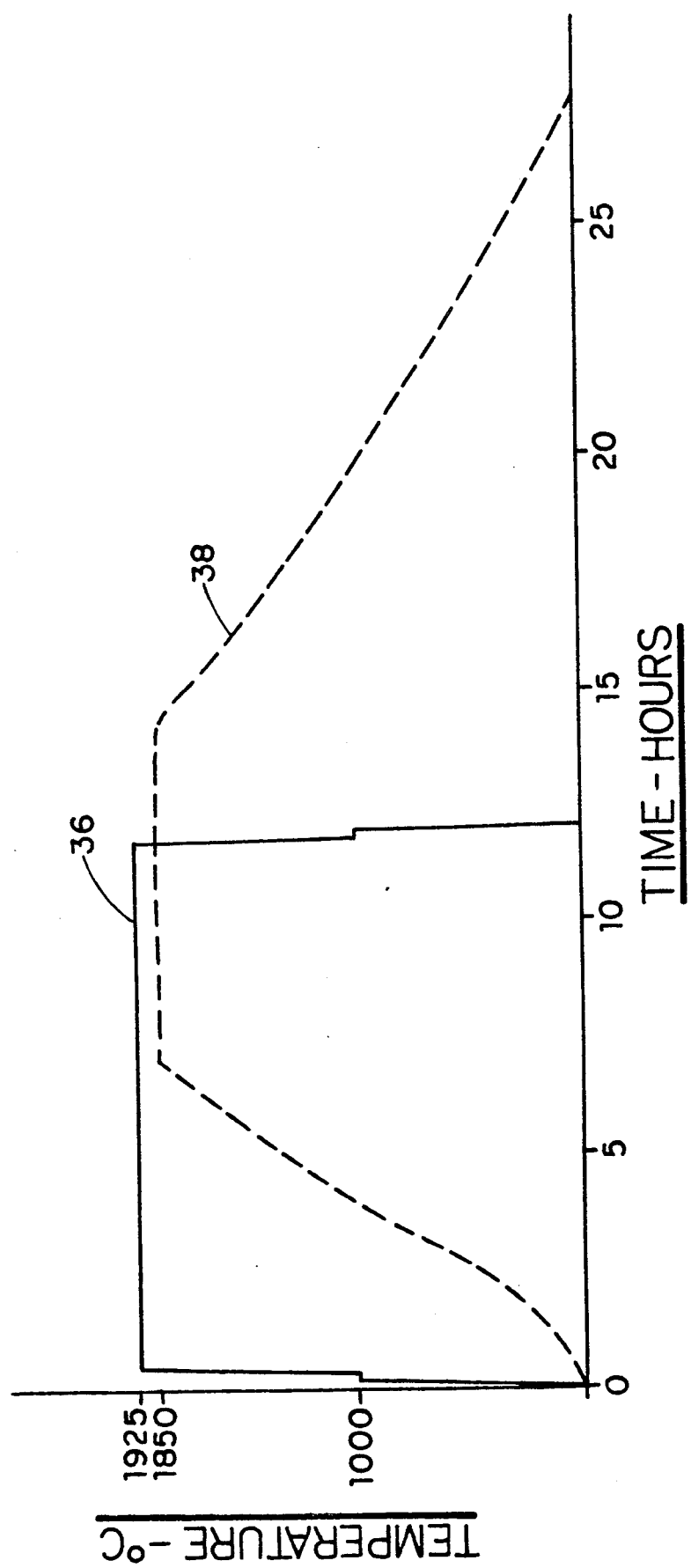
FIG. 7 is a graphical representation of a time versus temperature cure for a heat treatment process in accordance with the present invention versus a typical prior heat treatment process.

The heat treated specimens according to the present invention were heat treated in a hydrogen atmosphere at a temperature of about 1920° C. for a time period of about 12 hours. The specimens were taken out of the oven and allowed to cool to room temperature. Referring to FIG. 7, there is illustrated in graphical form the time versus temperature curve 36 (solid line) of bracket 10 heat treated in accordance with the present invention. As can be seen clearly from curve 36, the temperature of bracket 10 increases rapidly from room temperature to the heat treatment temperature of 1920° C. and is rapidly decreased back to room temperature.

The prior art heat treatment consisted of subjecting the specimens in an oven with a hydrogen atmosphere at a temperature of about 1850° C. for a time period of about 6 hours. Referring back to FIG. 7, the time versus temperature curve 38 (shown in dash lines) represents the temperature of the brackets subjected to a heat treatment process according to the prior art. The brackets 10 were placed in the staging area 26 adjacent inlet 22. The brackets were then slowly moved through the staging area 26 to hot zone 28 at the rate of about 4 inches per hour. The bracket after reaching the hot zone 28 was maintained in hot zone 28 for about 6 hours. Thereafter the brackets were moved into cooling zone 30 and allowed to cool to room temperature over an 18 hour period. From a comparison of heat treatment process curve 36 according to the present invention with respect to the prior art treatment curve 38 clearly illustrate the differences there between. First, the overall time necessary for the heat treatment of the prior art is substantially longer, secondly, the increase and decrease of the temperature of the brackets in the process according to the present invention is considerably faster as opposed to the slow process of the prior art.

The fracture toughness of the specimens as measured in Kic(MPa.m½) is set forth in the following table:

| Notches Formed by | Kic As Machined | Kic Prior Art Preheat Treatment | Kic Present Invention |
|---|---|---|---|
| Diamond Wheel | 2.3 ± 0.6 | 2.7 ± .04 | 3.8 ± 2.0 |
| Diamond Filing | 1.7 ± 0.3 | N/A | 2.0 ± .0 |
| Ultrasonic Machining | 4.1 ± .7 | N/A | 7.1 ± .07 |

With respect to the specimen formed by diamond filing, relatively small improvement was obtained. This is believed to be due to the fact that many of the flaws introduced by the diamond filing procedure are too large for the healing capabilities of the heat treatment process. However, specimens which were subjected to diamond wheel grinding obtained about a 78% improvement in Kic and specimens that were ultrasonically machined obtained improvement of about 142% of Kic. Thus, brackets made in accordance with the present invention showed a marked improvement in fracture toughness. This will, in turn, lead to improved resistance to breakage due to the brittle nature of the material from which the bracket is made.

In addition to the improved fracture toughness, applicants have found that the clarity of the crystalline bracket is also improved. This is particularily important with brackets made of a single crystalline material wherein asthetic is an important feature of the bracket.

Various changes and modifications may be made without departing from the scope of the present invention. The following claims setting forth the scope of the present invention.

What is claimed is:

1. A method of improving the fracture toughness of a crystalline orthodontic bracket which has been subject to at least one machining operation comprising the steps of:
   a) placing said crystalline orthodontic bracket in an oven and heating said bracket to thereby increase the temperature of said bracket to an elevated temperature above the normal annealing temperature of said crystalline orthodontic bracket and slightly below the melting point of said crystalline bracket, which temperature is capable of healing surface microcracks;
   b) maintaining said orthodontic bracket at said elevated temperature for a predetermined period of time for healing microcracks on the surface of said bracket; and
   c) cooling said orthodontic bracket at a predetermined rate to about room temperature.

2. A method of improving the fracture toughness of a crystalline orthodontic bracket which has been subject to at least one machining operation comprising:
   a) placing said bracket in an oven at an elevated temperature and heating said bracket at a rate no less than about 200° C./min.;
   b) thereby increasing the temperature of said bracket to an elevated temperature slightly below the melting point of said bracket, said temperature being above normal annealing temperature of said crystalline bracket and capable of healing surface microcracks;
   c) maintaining said bracket at said elevated temperature for a predetermined period of time so as to cause the microcracks on the surface of said bracket to heal; and
   d) cooling said bracket at a predetermined rate to about room temperature.

3. A method of improving the fracture toughness of a crystalline alumina orthodontic bracket which has been subject to at least one machining operation comprising the steps of:
   a) placing said crystalline alumina orthodontic bracket in an oven at an elevated temperature of at least 1875° C., but no greater than 1950° C. and heating said bracket to thereby increase the temperature of said bracket to an elevated temperature slightly below the melting point of said bracket, which elevated temperature is capable of healing surface microcracks;
   b) maintaining said crystalline orthodontic bracket at said elevated temperature for a predetermined period of time so as to heal microcracks on the surface of said orthodontic bracket; and
   c) cooling said crystalline orthodontic bracket at a rate no less than 100° C./min to about room temperature.

4. A method according to claim 3 wherein said crystalline orthodontic bracket is maintained at a temperature of about 1925° C.

5. A method according to claim 3 wherein the temperature of said orthodontic bracket is increased to said elevated temperature at a rate no less than 200° C./min.

6. A method according to claim 3 wherein said crystalline orthodontic bracket is maintained at said elevated temperature for a period of at least 4 hours.

7. A method according to claim 3 wherein said crystalline orthodontic bracket is maintained at an elevated temperature of about 1925° C. for about 6 hours.

8. A method of improving the fracture toughness of a crystalline alumina orthodontic bracket according to claim 3 wherein said crystalline alumina orthodontic bracket is maintained in said oven at a temperature of about 1925° C.

9. A method of improving the fracture toughness of a crystalline alumina orthodontic bracket according to claim 3 wherein said crystalline alumina orthodontic bracket is maintained in said oven at said elevated temperature for at least four hours.

10. A method of improving the fracture toughness of a single crystalline orthodontic bracket which has been subject to at least one machining operation comprising the steps of:
   a) placing said crystalline orthodontic bracket in an oven at an elevated temperature;
   b) heating said bracket to allow the temperature of said crystalline bracket to increase to an elevated temperature slightly below the melting point of said bracket and above the normal annealing temperature of said crystalline orthodontic bracket, which elevated temperature is capable of healing surface microcracks;

c) maintaining said orthodontic bracket at said elevated temperature for a predetermined period of time so as to heal microcracks on the surface of said bracket; and d) cooling said orthodontic bracket at a predetermined rate to about room temperature.

11. A method of improving the fracture toughness of a crystalline orthodontic bracket which has been subject to at least one machining operation comprising the steps of:

a) placing said crystalline bracket in an oven and rapidly heating said bracket to thereby increase the temperature of said bracket to an elevated temperature above normal annealing temperature of said crystalline orthodontic bracket and slightly below the melting point of said bracket, which temperature is capable of healing surface microcracks;

b) maintaining said bracket at said elevated temperature for a predetermined period of time for healing microcracks on the surface of said bracket; and c) rapidly cooling said bracket to about room temperature.

* * * * *